United States Patent [19]
Endo

[11] 4,207,790
[45] Jun. 17, 1980

[54] KNIFE HOLDER FOR MICROTOMES

[75] Inventor: Hidetoshi Endo, Seki, Japan

[73] Assignee: Feather Kogyo Kabushiki Kaisha, Mino, Japan

[21] Appl. No.: 966,043

[22] Filed: Dec. 4, 1978

[30] Foreign Application Priority Data

Dec. 6, 1977 [JP] Japan ................. 52-146478

[51] Int. Cl.$^2$ ................. B26D 7/26; G01N 1/06
[52] U.S. Cl. ................. 83/698; 83/915.5
[58] Field of Search .......... 83/698, 915.5, 870; 30/349, 344, 346.51, 346.58, 346.59

[56] References Cited

U.S. PATENT DOCUMENTS

| | | | |
|---|---|---|---|
| 3,699,830 | 10/1972 | Pickett | 83/915.5 X |
| 3,727,506 | 4/1973 | Taylor et al. | 83/915.5 X |
| 3,866,642 | 2/1975 | Walser | 83/870 X |

*Primary Examiner*—Frank T. Yost
*Attorney, Agent, or Firm*—Wenderoth, Lind & Ponack

[57] ABSTRACT

A microtome knife holder comprises a base plate and a holder plate for supporting a knife therebetween. The base plate has a wedge-shaped cross section having a first sharpened edge, the base plate having a stepped surface that extends along the first sharpened edge and on which the knife is locatable with its blade extending beyond the first sharpened edge. The base plate also has a groove extending parallel to and remotely from the stepped surface. The holder plate has a second sharpened edge and a flat surface extending along the second sharpened edge and facing to the stepped surface in spaced relation for sandwiching the knife between the flat and stepped surfaces, the holder plate further having a leg located remotely from the second sharpened edge and disposed in the groove in the base plate. A plurality of screws spaced from each other extend through the holder plate threadedly into the base plate and its portion which lies between the groove and the stepped surface. The base plate includes a shoulder which extends substantially at a right angle to the stepped surface and with which is engageable the edge of the knife that is remote from the blade.

5 Claims, 6 Drawing Figures

KNIFE HOLDER FOR MICROTOMES

BACKGROUND OF THE INVENTION

1. Field of the Invention

The present invention relates to a knife holder for microtomes.

2. Prior Art

There have been known in the past holders for supporting replaceable microtome knives. Since microtomes knives are fixedly mounted on such known holders simply by adhesive bonding, many difficulties have been experienced with the conventional holders. For example, the applied adhesive should be removed from the holder and the knife should be cleansed each time a spare knife is to be installed. The microtome cannot be operated to cut the object into specimen slices until the adhesive becomes sufficiently solidified to hold the knife in position on the holder. Further, the knife tends to be adhesive-bonded in an improper position and posture, with the results that sliced sections will have irregular thicknesses and roughened surfaces.

SUMMARY OF THE INVENTION

A microtome knife holder of the present invention comprises a base plate of a substantially wedge-shaped cross section and a holder plate screwed to the base plate for holding a knife between the holder and base plates. The base plate has a stepped surface that extends along its sharpened edge and on which a microtome knife is locatable with its blade extending beyond the sharpened edge of the base plate, the base plate including a shoulder along the stepped surface against which is held the edge of the knife that is remote from the blade. The holder plate has a raised surface extending along its one edge and positioned in face-to-face relationship to the stepped surface of the base plate, for firmly sandwiching the knife between the raised and stepped surfaces. The base plate has a groove extending parallel to and spaced from the stepped surface, and the holder plate has a leg remote from the raised surface, the groove receiving therein the leg for guiding the holder plate therealong. The holder plate is fixed to the base plate by means of screws extending through the holder plate threadedly into threaded holes in the base plate that are disposed between the groove and the stepped surface.

An object of the present invention is to provide a knife holder for microtomes which allows a used knife to be easily replaced by a new one.

Another object of the present invention is to provide a knife holder for microtomes which can cooperate with conventional spare knife dispensers for easy and simple knife replacement.

Still another object of the present invention is to provide a microtome knife holder for holding a knife correctly and reliably.

The above and other objects and advantages of the present invention will become apparent from the following description which, when taken in conjunction with the accompanying drawings, shows a preferred embodiment by way of illustrative example.

DETAILED DESCRIPTION OF THE PREFERRED EMBODIMENTS

Figure 1:
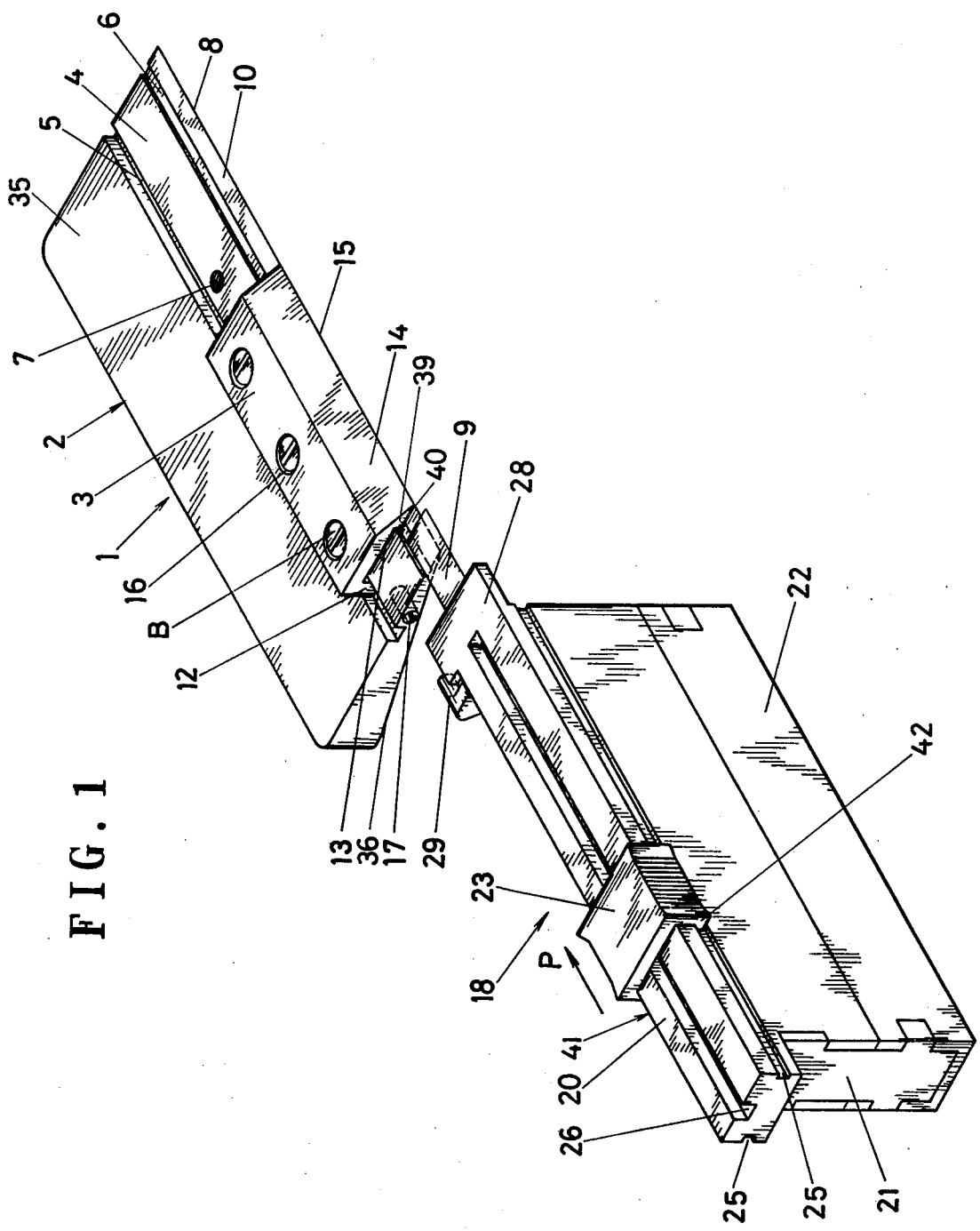
FIG. 1 is a perspective view of a microtome knife holder constructed in accordance with the present invention and a spare knife dispenser to be associated with the knife holder.

As shown in FIG. 1, a knife holder 1 for microtomes which is provided according to the present invention generally comprises a base plate 2 and a holder plate 3. The base plate 2 is composed of an elongated body of a substantially wedgeshaped cross-section. The base plate 2 has a pair of upper and lower surfaces 35, 36 that extend at a sharp angle to each other and jointly provide a sharpened edge 8 where they meet together, the edge 8 extending along the base plate 2. The base plate 2 has in its upper surface 35 a first groove 6 extending along but spaced a predetermined distance from the sharpened edge 8, and a second groove 5 extending parallel to and remote from the sharpened edge 8. An elongated portion 4 of the upper surface 35 is bounded between the first and second grooves 6, 5 and acts as a guide for the holder plate 3. A plurality of threaded holes 7 (only one shown in FIG. 1) are disposed in the surface portion 4.

Figure 2:
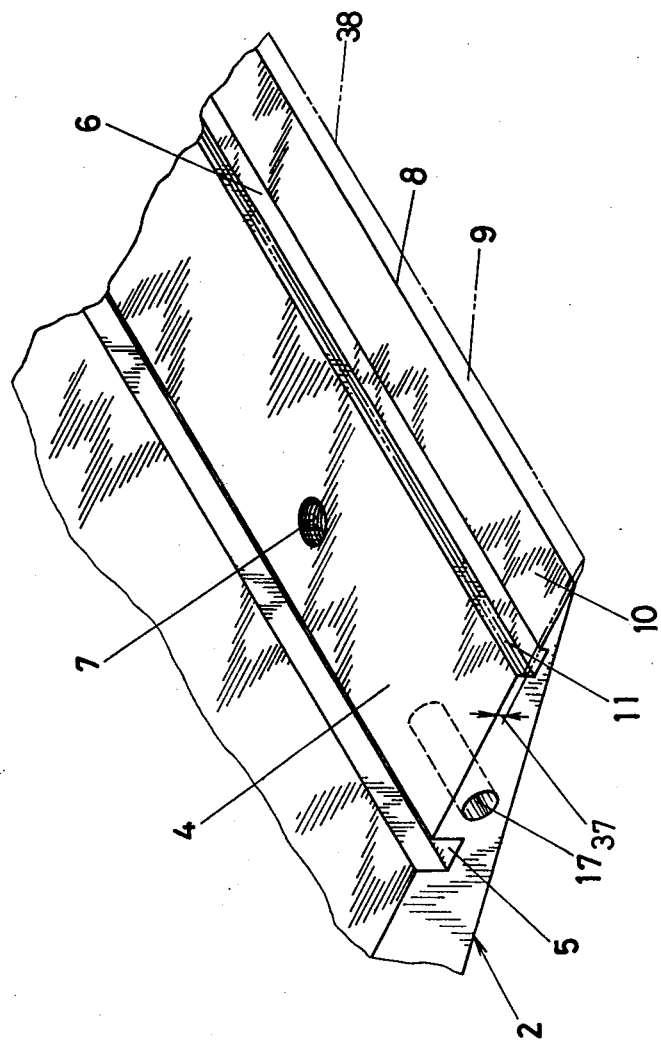
FIG. 2 is an enlarged fragmentary perspective view of the knife holder of FIG. 1.
Figure 3:
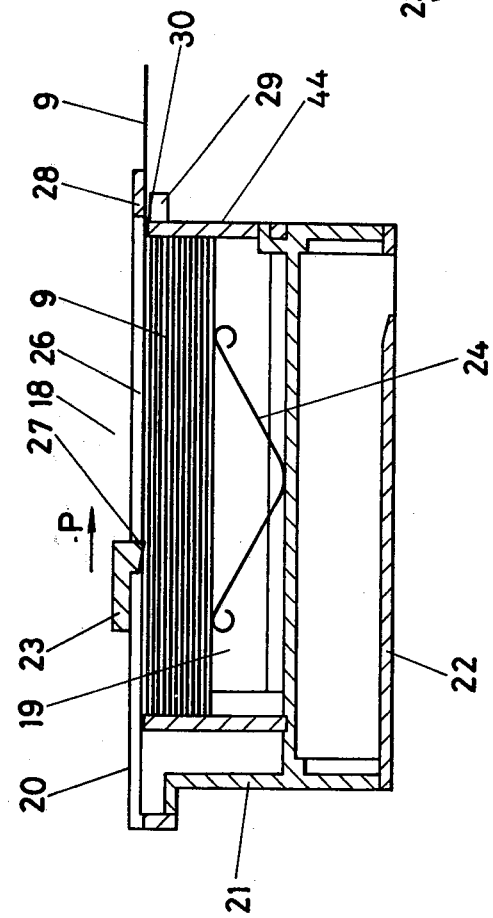
FIG. 3 is a vertical cross-sectional view of the dispenser of FIG. 1.
Figure 4:
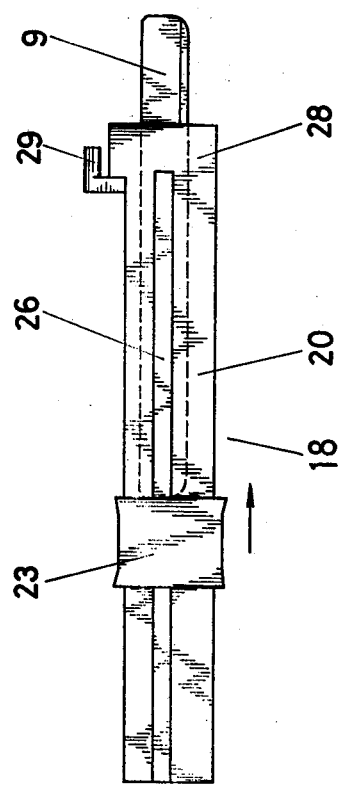
FIG. 4 is a plan view of the dispenser.

Between the first groove 6 and the sharpened edge 8, there extends a stepped surface 10 extending parallel to and offset a preselected distance 37 from the surface portion 4, as best shown in FIG. 2, such preselected distance 37 being preferably greater than the thickness of a knife to be supported on the knife holder 1. The stepped surface 10 acts as a support on which a knife 9 rests with its blade 38 disposed beyond the sharpened edge 8 of the holder plate 2. A sidewall 11 of the groove 6 extends substantially at a right angle with respect to the stepped surface 10 and serves as a shoulder with which there is engagable the edge of the knife 9 that is remote from the blade 38. The groove 6 is preferably formed as by a milling cutter, grooving tool so as to make the sidewall 11 as flatwise as possible for neat contact with the edge of the knife 9.

In FIG. 1, the holder plate 3 is of a rectangular configuration and has a slanted surface 14 extending therealong for facilitating the cutting off of specimen slices on the knife blade. The slanted surface 14 terminates at its one side in a sharpened edge 15 which extends substantially along the sharpened edge 8 of the base plate 2. The holder plate 3 has a leg 12 extending parallel to and located remotely from the sharpened edge 15, the leg 12 being slidably disposed in the groove 5 in the base plate 2. The holder plate 3 has a land 39 having a flat surface 40 that extends along the sharpened edge 15 and faces to the stepped surface 10 of the base plate 2 in parallel spaced relation. The knife 9 can be held in position between the flat surface 40 and the stepped surface 10. Between the leg 12 and the land 39, there is a recess 13 in which the surface portion 4 of the base plate 2 rides for the guidance of the holder plate 3 therealong. With such an arrangement, the distance between the leg 12 and the sharpened edge 15 of the holder plate 3 is substantially equal to that between the groove 5 and the sharpened edge 8 of the base plate 2. The holder plate 3 has a plurality of through holes 16 through which bolts B extend threadedly into the threaded holes 7 in the base plate 2. In the illustrated embodiment, the number of the holes 16 is three and the number of the threaded holes 7 is four, the threaded holes 7 being spaced from each other at intervals that are equal to the intervals at which the holes 7 are spaced from each other. Thus, the holder plate 3 can be fixed at selected positions on the base plate 2 so as to make the knife holder 1 adaptable for use on a variety of types of microtomes, such as rotary microtomes or sliding microtomes. For instance, the holder plate 3 is located at the position shown in FIG. 1 for use on a sliding microtome. The base plate 2 has a blind hole 17 in its one end wall.

As illustrated in FIG. 1, a spare knife is supplied from a spare knife dispenser 18 to the knife holder 1. In FIGS. 1, 3, 4 and 5, the dispenser 18 comprises a body 41 having therein a spare knife storing chamber 19 and a used knife storing chamber 22, the body 41 being closed off by a pair of end walls 20 having a longitudinal slot 26 and a pair of side grooves 25, extending parallel to the slot 26, there being a slide 23 including a pusher 27 disposed in the slot 26 and a pair of opposed guide lips 42 slidably fitted in the side grooves 25, respectively. A leaf spring 24 is disposed in the spare knife storing chamber 19 and acts on a stack of the spare knives 9 within the chamber 19 to urge them against the top plate 20. The top plate 20 has at one end an extension 28 acting as a knife guide. The dispenser body 41 has a slit 30 located beneath the top plate extension 28 for the passage therethrough of an uppermost one of the spare knives 9. The body 41 also has a pin 29 near the extension 28, the pin 29 being insertable into the hole 17 in the holder base plate 2 for positioning the dispenser 18 stationarily with respect to the knife holder.

When it is necessary to replace the used knife on the holder 1 with a spare knife, the bolts B are first loosened to release a grip on the used knife under the holder plate 3. The pin 29 on the dispenser 18 is inserted into the hole 17 in the holder 1 and the knife guide 28 is placed onto the upper surface 35 of the base plate 2 so as to hold the dispenser 18 immovably with respect to the holder 1. Then, the slide 23 is slid from its stroke end near the end wall 21 in the direction of the arrow P toward the knife guide 28, thereby enabling the pusher 27 to engage and push the uppermost spare knife 9 out of the sotrage chamber 19 through the slit 30. The spare knife as it is discharged from the dispenser 18 is slid on and along the stepped surface 10 of the base plate 2 and under the land 39 of the holder plate 3. At this time, the old knife is pushed out of the holder 1 endwise by the new knife being installed. Upon arrival of the slide 23 at its stroke end near the knife guide 28, the transfer of the spare knife 9 is completed, and the spare knife dispenser 18 is separated from the holder 1. The bolts B are tightened again to grip the knife 9 tightly between the base plate 2 and the holder plate 3 with the edge of the knife 9 which is remote from the blade 38 being held against the shoulder 11. With the uppermost spare knife removed, a next spare knife in the dispenser 18 comes up under the force from the leaf spring 24 and is held against the top plate 20 so as to be ready for being discharged by the slide 23 out of the dispenser 18.

Figure 6:
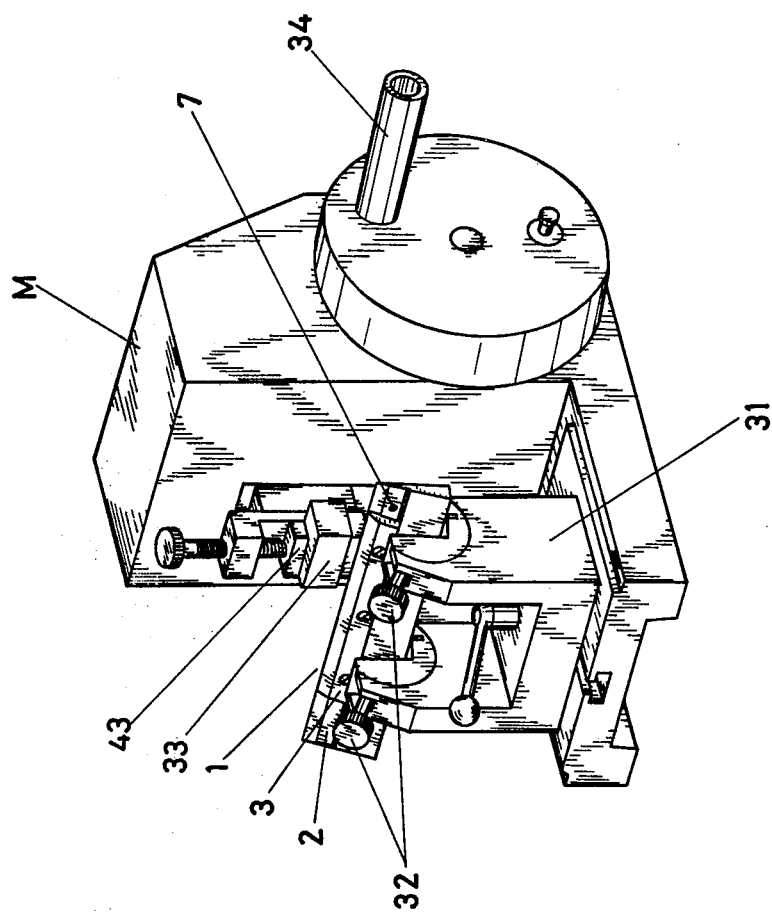
FIG. 6 is a perspective view of a rotary microtome equipped with the knife holder of the invention.
Figure 5:
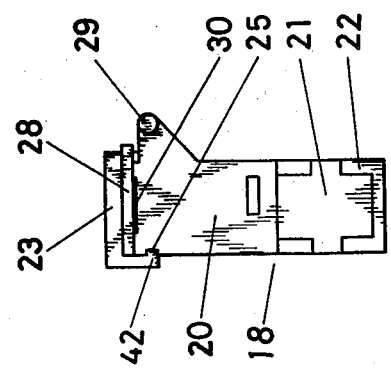
FIG. 5 is a side elevational view of the dispenser.

The knife holder 1 with the new knife 9 thus mounted thereon is supported on a pair of mount arms 31, disposed on a microtome M (FIG. 6) which is shown herein as a rotary microtome, the holder 1 being fixed relatively to the mount arms 31 by a pair of screws 32, respectively. In order for the holder 1 to be used on the rotary microtome M, the holder plate 3 is shifted one threaded hole 7 from the position of FIG. 1. A specimen block 33 supported on a clamp 43 is lowered by rotation of a handle lever 34 and is cut into slices suitable for examination under the microscope.

The spare knives to be supported on the holder 1 are made of stainless steel with a coating of chrome alloy on the blade. The knife surfaces are coated with resin of ethylene tetrafluoride for an increased degree of blade sharpness and durability to meet the requirements necessary for use as microtome knives.

Although the preferred embodiment of the invention has been shown and described in detail, it should be understood that various changes and modifications may be made therein without departing from the scope of the appended claims.

I claim:

1. A knife holder comprising:
   a base plate of a substantially wedge-shaped cross-section having a first sharpened edge, said base plate having a stepped surface that extends along said first sharpened edge and on which a knife is locatable with its blade extending beyond said first sharpened edge, said base plate having a groove extending parallel to and remotely from said stepped surface;
   a holder plate having a second sharpened edge and a flat surface extending along said second sharpened edge and facing to said stepped surface in spaced relation for sandwiching the knife between said flat and stepped surfaces, said holder plate having a leg located remotely from said second sharpened edge and disposed in said groove in the base plate; and,
   a plurality of screws spaced from each other and extending through said holder plate threadedly into a portion of said base plate which lies between said groove and said stepped surface.

2. A knife holder according to claim 1, said base plate including a shoulder which extends substantially at a right angle to said stepped surface and with which there is engagable the edge of the knife that is remote from the blade.

3. A knife holder according to claim 1, the distance between said leg and said second sharpened edge of said holder plate being substantially equal to that between said groove and said first sharpened edge of said base plate.

4. A knife holder according to claim 1, said stepped surface extending substantially parallel to said flat surface.

5. A knife holder according to claim 1, said holder plate including a land having said flat surface.

* * * * *